United States Patent
Hu et al.

(10) Patent No.: US 11,667,880 B2
(45) Date of Patent: Jun. 6, 2023

(54) SINGLE-USE PH SENSOR FOR BIOREACTOR APPLICATIONS

(71) Applicant: Rosemount Inc., Shakopee, MN (US)

(72) Inventors: Jinbo Hu, Minneapolis, MN (US); Andrew S. Dierker, Minnetonka, MN (US); Rick J. Sumrall, Eden Prairie, MN (US); Tyrel L. Ruch, Saint Paul, MN (US); John W. Simon, Burnsville, MN (US); Ryan L. Bowlds, Chanhassen, MN (US)

(73) Assignee: ROSEMOUNT INC., Shakopee, MN (US)

( * ) Notice: Subject to any disclaimer, the term of this patent is extended or adjusted under 35 U.S.C. 154(b) by 0 days.

(21) Appl. No.: 17/194,686

(22) Filed: Mar. 8, 2021

(65) Prior Publication Data
US 2021/0189319 A1    Jun. 24, 2021

Related U.S. Application Data

(62) Division of application No. 16/277,169, filed on Feb. 15, 2019, now Pat. No. 11,046,927.
(Continued)

(51) Int. Cl.
*G01N 27/403* (2006.01)
*C12M 1/34* (2006.01)
(Continued)

(52) U.S. Cl.
CPC .......... *C12M 41/26* (2013.01); *C12M 23/28* (2013.01); *G01N 27/302* (2013.01); *G01N 27/333* (2013.01)

(58) Field of Classification Search
CPC .......... G01N 27/403; G01N 27/4035; G01N 27/333; G01N 27/302
See application file for complete search history.

(56) References Cited

U.S. PATENT DOCUMENTS 8,631,716 B2    1/2014   Bernard et al.
8,640,560 B2    2/2014   Burke
(Continued)

FOREIGN PATENT DOCUMENTS

EP    709669 A1    5/1996
EP    0753737 A2   1/1997
(Continued)

OTHER PUBLICATIONS

Measuring Control Sensor Technology ProMinent Product Catalogue vol. 2, Heidelberg . Jan. 2017, 290 pages (Year: 2017).*
(Continued)

*Primary Examiner* — Alexander S Noguerola
(74) *Attorney, Agent, or Firm* — Christopher R. Christenson; Kelly, Holt & Christenson, PLLC

(57) ABSTRACT

A pH sensor for a single-use container includes a plunger sleeve configured to couple to a flange of the single-use container. A plunger is axially movable within the plunger sleeve between a storage position and an operating position. A pH sensing element coupled to the plunger wherein the pH element is disposed within a storage chamber in the storage position and is configured to be exposed to an interior of the single-use container in the operating position. In one example, a temperature sensitive element is disposed within the pH sensor and configured to sense temperature proximate the pH sensing element. In another example, a lock member is coupled to the plunger, where the lock member has a locked position and an unlocked position, the lock member being configured to inhibit movement of the plunger when in the locked position. In yet another example, the plunger includes at least one filling channel that allows access to a reference fill chamber when the plunger is in a filling position.

17 Claims, 8 Drawing Sheets

Related U.S. Application Data

(60) Provisional application No. 62/636,334, filed on Feb. 28, 2018.

(51) Int. Cl.
  *C12M 1/00* (2006.01)
  *G01N 27/30* (2006.01)
  *G01N 27/333* (2006.01)

(56) References Cited

U.S. PATENT DOCUMENTS

| | | |
|---|---|---|
| 8,900,855 B2 | 12/2014 | Feng et al. |
| 9,056,695 B2 | 6/2015 | Bernard et al. |
| 9,868,930 B2 | 1/2018 | Adkins et al. |
| 11,046,927 B2 * | 6/2021 | Hu ............ C12M 23/14 |
| 2008/0283399 A1 | 11/2008 | Feng et al. |
| 2012/0240686 A1 | 9/2012 | Blomberg et al. |
| 2017/0218320 A1 | 8/2017 | Pizzi et al. |
| 2017/0299546 A1 | 10/2017 | Rutz et al. |

FOREIGN PATENT DOCUMENTS

| | | | |
|---|---|---|---|
| GB | 2093193 A * | 2/1981 | ............ G01N 27/30 |
| JP | 2001-242134 A | 9/2001 | |
| JP | 2004-157015 A | 6/2004 | |
| JP | 2017-117482 A | 6/2017 | |
| KR | 100874779 B1 | 12/2008 | |
| WO | 2009059645 A1 | 5/2009 | |

OTHER PUBLICATIONS

First Examination Report dated Jun. 5, 2021 for Indian Patent Application No. 202027038037, 6 pages including English translation.

Office Action dated Jul. 12. 2022, for Japanese Patent Application No. 2020-545096, 7 pages including English translation.

First Office Action dated Jul. 27, 2022, for Chinese Patent Application No. 201980016084.9, 19 pages including English translation.

Office Action for Russian Application No. 2020129837, dated Mar. 17, 2021, 15 pages including English translation.

Second Examination Report dated Sep. 15, 2021 for Australian Patent Application No. 2019227731, 3 pages.

Extended Search Report dated Nov. 5, 2021 for European Patent Application No. 19760387.1, 7 pages.

Office Action dated Dec. 7, 2021, for Japanese Patent Application No. 2020-545096, 11 pages including English translation.

* cited by examiner

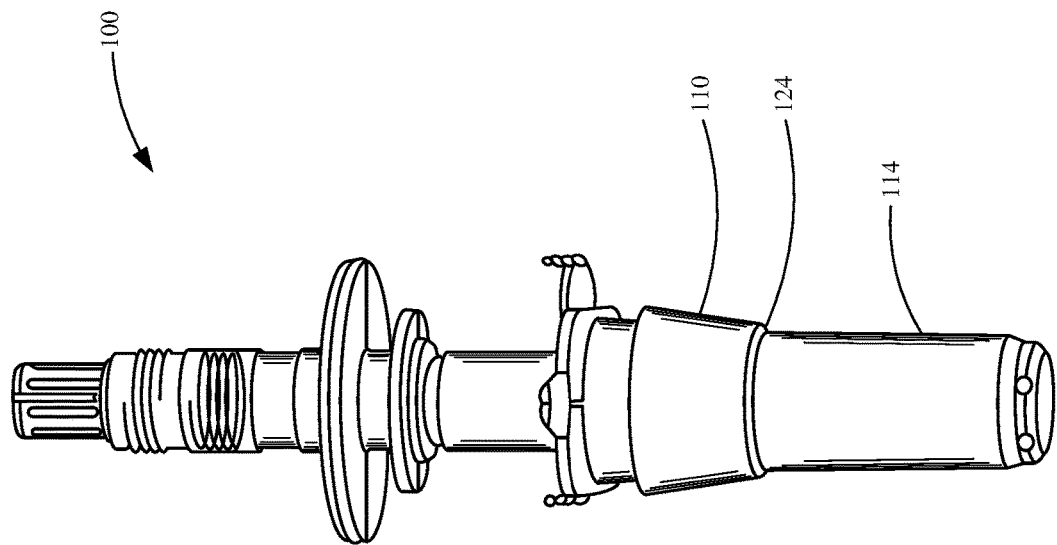
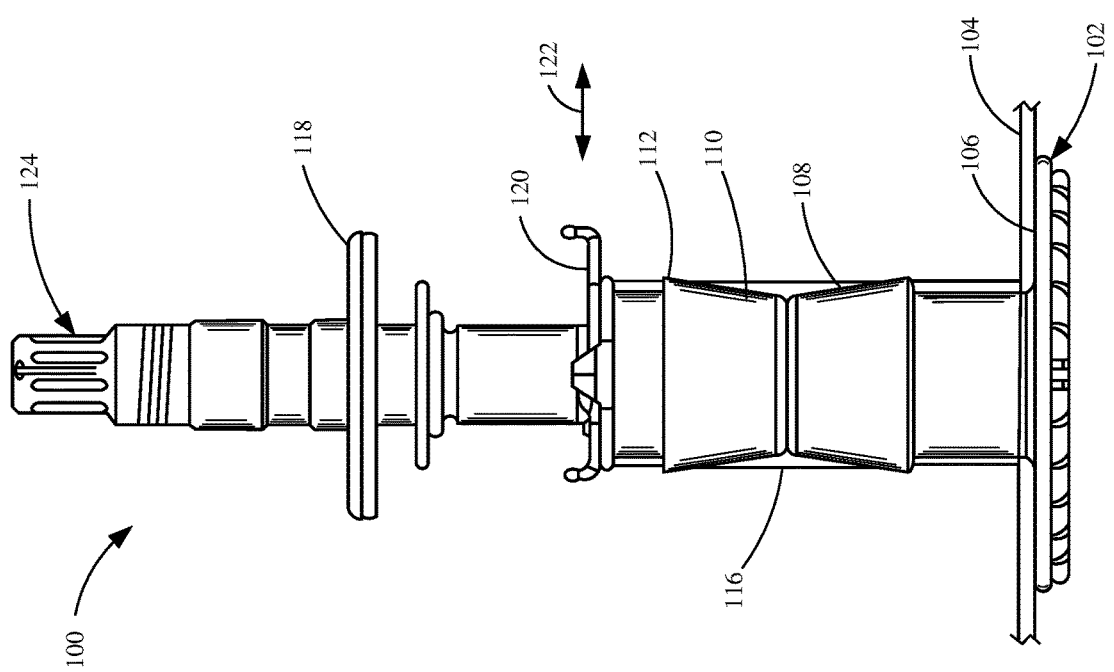

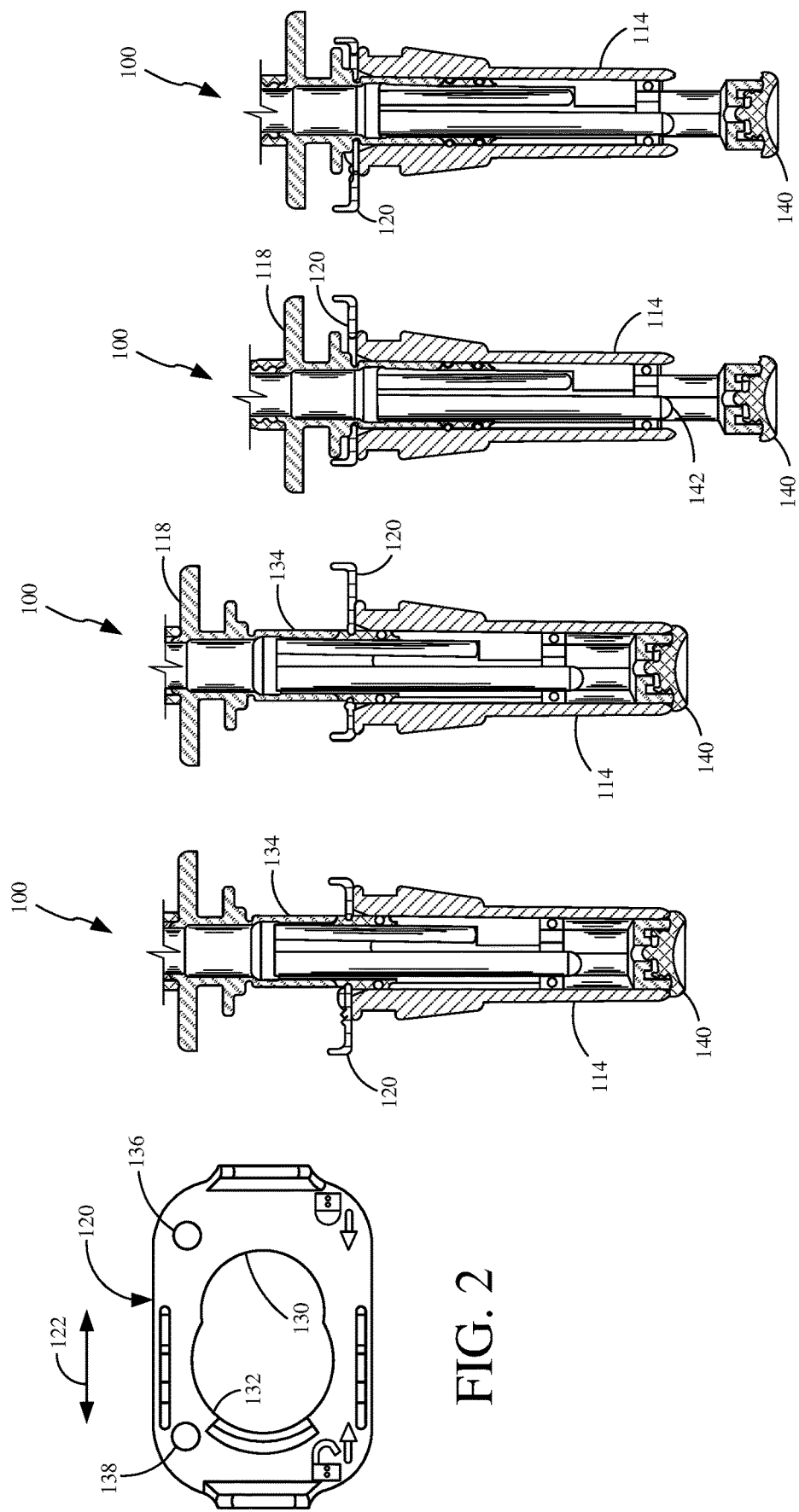

US 11,667,880 B2

SINGLE-USE PH SENSOR FOR BIOREACTOR APPLICATIONS

CROSS-REFERENCE TO RELATED APPLICATION

The present application is a divisional of U.S. non-provisional patent application Ser. No. 16/277,169, filed on Feb. 15, 2019 which is based on and claims the benefit of U.S. provisional patent application Ser. No. 62/636,334, filed Feb. 28, 2018, the content of which is hereby incorporated by reference in its entirety.

BACKGROUND

The determination of pH is one of the most common process chemical measurements today. pH is a measure of a relative amount of hydrogen and hydroxide ions in an aqueous solution. In fermentation and cell culture, one of the most critical process challenges is to maintain the optimal pH level. Fermentation processes utilize a live organism, such as a yeast, bacteria, or fungus strain to produce an active ingredient. Fermentation processes normally have a relatively short duration (2-7 days). Cell culture is a process in which a mammalian cell is grown to produce an active ingredient. The cell culture process typically takes somewhat longer (2-8 weeks).

One significant challenge for pH measurement in the fermentation and cell culture fields is the cleaning processes involved with the fermenter or bioreactor. Specifically, the fermenter or bioreactor must be sterilized prior to the beginning of either process to ensure against cross batch contamination or any unwanted growths. In addition, pH sensors typically undergo a two-point calibration using buffer solutions. The residual buffer chemicals must be removed prior to the beginning of a fermentation or culture batch. Such cleaning can include steaming the fermenter or bioreactor as well as the pH sensor. Exposure to high temperatures, steam and rapid thermal shock can significantly affect the sensor's life.

The life sciences industry is moving away from large, capital intensive facilities made of stainless steel with large clean in place (CIP) infrastructure and toward smaller facilities utilizing polymer-based bags or containers functioning as single-use bioreactors. A single-use bioreactor bag can be used once and then discarded. Using single-use bioreactors can significantly reduce the capital cost required for a plant. For example, in existing facilities using stainless steel CIP infrastructure, up to 90% of operating costs may be related to CIP infrastructure, including high-end instrumentation designed to withstand a steam cleaning cycle. By moving to disposable single-use bioreactor bags, the CIP portion of capital costs can be eliminated, facilities can be flexible and much smaller, which, in turn, allows the production of smaller batches that are needed, for example, for more targeted drug therapies and other small-scale applications.

A single-use pH sensor is described in U.S. Pat. No. 8,900,855. The sensor described in that patent is a single-use pH sensor that is suitable for bioreactors. The sensor can be attached to the wall of a single-use bioreactor bag, with a compartment configured to house a single-use pH sensor based on a glass pH electrode. During storage, the glass electrode is immersed in a storage buffer solution. Upon activation, the pH sensor is one-point calibrated against the known pH value of the storage buffer solution, and then pushed in to the bioreactor bag to an operating position through a sliding mechanism. The present disclosure provides a number of improvements over the sensor described in the '855 patent.

SUMMARY

A pH sensor for a single-use container includes a plunger sleeve configured to couple to a flange of the single-use container. A plunger is axially movable within the plunger sleeve between a storage position and an operating position. A pH sensing element coupled to the plunger wherein the pH element is disposed within a storage chamber in the storage position and is configured to be exposed to an interior of the single-use container in the operating position. In one example, a temperature sensitive element is disposed within the pH sensor and configured to sense temperature proximate the pH sensing element. In another example, a lock member is coupled to the plunger, where the lock member has a locked position and an unlocked position, the lock member being configured to inhibit movement of the plunger when in the locked position. In yet another example, the plunger includes at least one filling channel that allows access to a reference fill chamber when the plunger is in a filling position.

BRIEF DESCRIPTION OF THE DRAWINGS

FIG. 1A is a diagrammatic view of a pH sensor coupled to a bioreactor bag flange in accordance with an embodiment of the present invention.

FIG. 1B is a diagrammatic view of a pH sensor in accordance with an embodiment of the present invention.

FIG. 2 is a diagrammatic view of a slide lock of a pH sensor in accordance with an embodiment of the present invention.

FIGS. 3A-3D are diagrammatic views illustrating various locked/unlocked storage/operation positions of a pH sensor in accordance with an embodiment of the present invention.

DETAILED DESCRIPTION OF ILLUSTRATIVE EMBODIMENTS

Figure 4B:
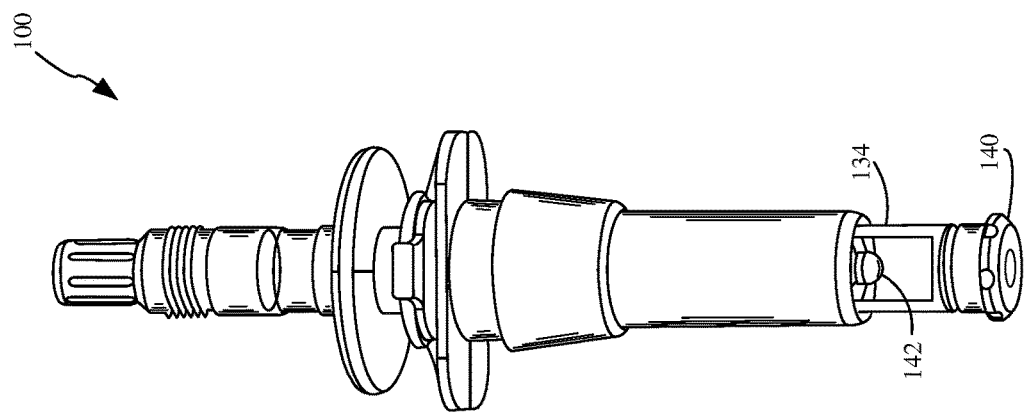
FIGS. 4A and 4B illustrate a pH sensor at its operating position both with an attachment to a bioreactor flange (FIG. 4A) and without an attachment to a bioreactor flange (FIG. 4B).

Temperature is an important parameter that affects pH measurements by changing the theoretical response of the pH sensing glass electrode. During the calibration operation, the pH sensor is still in storage position where the glass electrode is outside the bioreactor. The process temperature inside the bag is usually controlled at a constant temperature, such as 36.5 C, whereas the attached pH sensor is exposed to room temperature (usually 20-25 C) without a concise control mechanism. This creates a temperature gradient throughout the pH sensor, so that the temperature of the calibrating storage buffer solution is unknown and not predictable. This can lead to errors in sensor calibration.

During sensor operation, the glass electrode is pushed into the bioreactor process. However, the local temperature close to the electrode and the temperature of the bioreactor thermometer can be different. Therefore, to ensure an accurate temperature compensation, temperature measurement of the glass electrode is preferred. This is especially important when the glass bulb is close to the wall of the bioreactor bag, which may lead to a different temperature than the center of the bag. Accordingly, at least one aspect of the present invention provides a temperature sensitive element within the pH sensor assembly preferably proximate the glass bulb. The temperature sensitive element can be any suitable device that has an electrical characteristic that changes with temperature. Examples include, without limitation, resistance temperature devices (RTDs), thermocouples, thermistors, et cetera.

During sensor operation, the glass electrode portion may be pushed back from its operating position to the storage position by the internal pressure of the bag. This generates risk of sensor de-activation during its operation. In order to address this situation, at least one embodiment of the present invention provides a locking mechanism configured to prevent the pH sensor from being moved out of the operating position.

At least some embodiments disclosed herein provide a pH sensor with improved manufacturability. There are generally two sealed cavities in the pH sensor assembly that need to be filled with solutions without leaving air bubbles that can possibly lead to sensor failure by creating open circuits. Some embodiments provide a method to fill those two cavities without generating air bubbles. This may improve manufacturing speed and yield when such pH sensors are produced at a large scale.

Accordingly, embodiments of the present invention generally include one or more of the features set forth above. The design is illustrated with respect to the various figures.

FIG. 1A is a diagrammatic side view of a pH sensor coupled to a bioreactor bag flange in accordance with an embodiment of the present invention. pH sensor 100 is illustrated coupled to bioreactor bag flange 102, which is coupled to a bioreactor wall 104 at interface 106. Bioreactor bag flange 102 includes a hose barb fitting 108. Additionally, a coupling portion 110 of pH sensor preferably includes a hose barb 112. When plunger sleeve 114 (shown in FIG. 1B) is inserted into hose barb fitting 108, the hose barb 112 of coupling portion 110 is positioned adjacent hose barb 108 of bioreactor bag flange 102. A plastic or polymeric tube 116 is positioned over hose barbs 112, 108 to secure pH sensor 100 to bioreactor bag flange 102. The plastic tubing also seals the pH sensor 100 to bioreactor bag flange 102. Plastic tubing 116 can be further secured by the use of zip ties or other suitable fasteners.

As shown in FIG. 1A, pH sensor 100 includes a plunger flange 118 that allows the end user to push the plunger into the bioreactor process to activate pH sensor 100 to its operating position. pH sensor 100 also includes a slide lock 120 movable in the direction of arrows 122 to provide a locked or unlocked position. When in the unlocked position, pH sensor 100 is movable axially into or out of the bioreactor bag. Conversely, when slide lock 120 is in the locked position, pH sensor is not axially movable relative to bag flange 102 or the bioreactor bag.

FIG. 1A also shows pH sensor 100 including an electrical connector 124 at an end that is opposite plunger sleeve 114. In one example, connector 124 is a variopin (VP), which is a multipin connector that that allows simultaneous communication of pH signals as well as temperature signals. Further, the VP connector 124 is also sealed even when in an unconnected condition.

FIG. 1B is a diagrammatic perspective view of a pH sensor in accordance with an embodiment of the present invention. In FIG. 1B, sensor 100 is shown without bag flange 102 (shown in FIG. 1A). Plunger sleeve 114 is substantially cylindrical in shape having a diameter that is smaller than that of coupling portion 110. This arrangement allows shoulder 124 to bear against hose barb 108 of bag flange 102 to create a positive axial stop when plunger sleeve is inserted into hose barb fitting 108. Such stop helps create a repeatable axial position of pH sensor relative to the bioreactor bag flange 102.

FIG. 2 is a diagrammatic view of slide lock 120 showing its use during storage and operating positions. As shown in FIG. 2, slide lock 120 includes a pair of interconnected holes 130, 132 having different outer diameters. Hole 132 is sized to allow axial movement of plunger 134 (shown in FIGS. 3A-3D). Conversely, hole 130 is sized to prevent axial movement of plunger 134 via a friction or interference fit or via a cooperative engagement with a groove or structure on plunger sleeve 114. The locked/unlocked position of slide lock 120 can be switched by sliding in the direction of arrow 122. This provides a mechanism of locking the movement of plunger 134 both at storage and operation positions, thus preventing unwanted activation or de-activation of the pH sensor. Slide lock 120 also provides two holes 136, 138 for lockout/tagout to prevent undesired sliding.

FIGS. 3A-3D are diagrammatic views illustrating various locked/unlocked storage/operation positions of a pH sensor in accordance with an embodiment of the present invention. FIG. 3A shows pH sensor 100 locked in a storage position. The locking position can be identified by slide lock 120 being located in a left-most position. Additionally, the storage position can be identified by end 140 being positioned against plunger sleeve 114. FIG. 3B shows pH sensor 100 in an unlocked storage position. As can be seen, end 140 is still positioned against plunger sleeve 114, but slide lock 120 has been slid from the left-most position (shown in FIG. 3A) to the right-most position. Thus, plunger 134 is axially movable in FIG. 3B.

FIG. 3C shows pH sensor 100 in an unlocked operating position. In comparison to FIG. 3B, slide lock 120 is still in the same position. However, plunger flange 118 is closer to slide lock 120 in FIG. 3C than in FIG. 3B. Further, plunger 134 has moved axially into the bioreactor bag causing end 140 to be spaced from plunger sleeve 114. This allows the contents of the bioreactor to contact pH sensing bulb 142 to obtain a pH value of the bioreactor contents. FIG. 3D shows pH sensor 100 locked in an operating position as slide lock 120 has been returned to its left-most position. In this position, plunger 134 is prevented from moving axially and thus maintains the spacing between end 140 and plunger sleeve 114. While FIGS. 3A-3D provide one example of a locking mechanism, those skilled in the art will recognize that a variety of mechanisms can be employed to selectively inhibit axial movement.

Figure 4A:
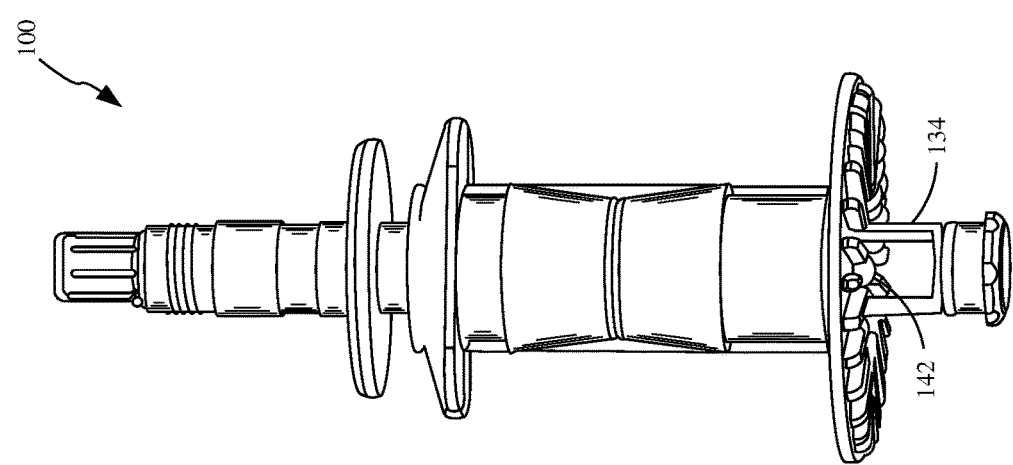

FIGS. 4A and 4B illustrate pH sensor 100 at its operating position (FIG. 4A) and without attachment to the bioreactor bag flange (FIG. 4B). FIGS. 4A and 4B show pH sensor in its operating position. At this position, plunger 134 together with the storage solution has been pushed out into the process (i.e. the interior of the bioreactor), so that pH glass electrode 142 and the reference junction (shown in FIGS. 5A and 5B) are exposed to the process. The end of plunger 134 is designed to be open, which allows air bubbles in the process to travel through, thus reducing the risk of air bubbles accumulating on pH glass electrode 142 or the reference junction.

Figure 5A:
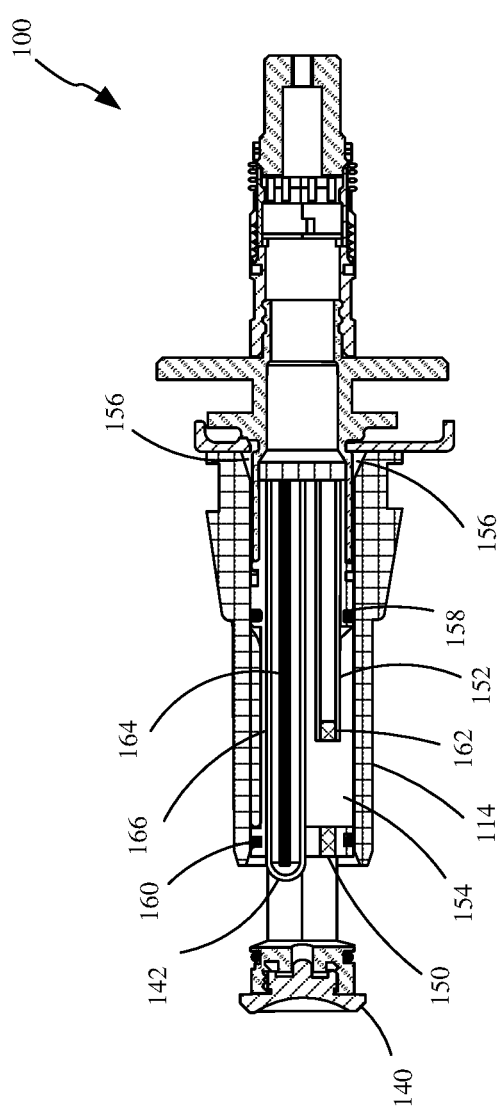
FIGS. 5A and 5B are cross-sectional views of a pH sensor in an operating and storage positions, respectively.
Figure 5B:
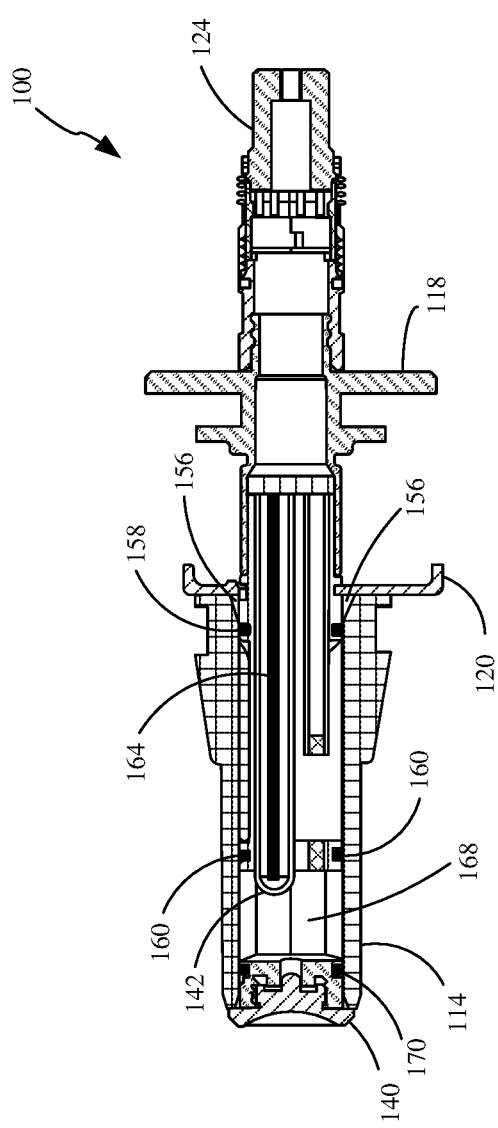

FIGS. 5A and 5B are cross-sectional views of one embodiment of a pH sensor in an operating and storage positions, respectively. In FIG. 5A, end 140 is spaced from plunger sleeve 114 thereby placing pH sensor 100 in an operating position. In this position, sample fluid (e.g. process fluid or bioreactor contents) contacts pH glass electrode 142 as well as reference junction 150 of reference electrode 152. Reference junction 150 may be formed of a ceramic and has sufficient porosity to support the flow of ions from reference fill cavity 154 into the process. Reference fill cavity 154 is filled with a suitable liquid or gelled electrolyte, such as KCl or Ag/KCl. Reference fill liquid is introduced into reference fill cavity 154 via one or more reference fill channels 156. The reference fill liquid is substantially sealed within reference fill cavity 154 via a pair of sealing elements (e.g. o-rings) 158, 160. Reference fill cavity 154 is filled through two reference fill channels 156 that are located at the end of the plunger sleeve 114, and the filling operation is illustrated with respect to FIGS. 6A and 6B.

Electrode 152 is preferably a double junction reference electrode having reference junction 162 and reference junction 150. Reference junction 162, like reference junction 150 has sufficient porosity to support the flow of ions between reference fill cavity 154 and an interior of electrode 152. Double junction reference electrode 152 is so termed due to the pair of reference junctions 150, 162 through which ions flow during pH measurement. In one embodiment, reference electrode 152 is based on a silver/silver chloride wire (not shown) that is protected by a glass tubing and two ceramic reference junctions 162, 150. One reference junction 162 is located at the end of the glass tubing and the second junction 150 is located between the reference fill cavity 154 and storage fill solution cavity 168 (shown in FIG. 5B) to isolate the two cavities, protecting reference electrode 152 from being fouled or poisoned by the bioreactor process.

As shown in FIGS. 5A and 5B, pH sensor 100 includes a temperature sensitive element 164 disposed within glass tube 166 of pH glass electrode 142. Temperature sensitive element may be any suitable structure that has an electrical characteristic that varies with temperature. Examples include, without limitation, resistance temperature devices (RTDs, thermocouples, thermistors, et cetera). Placing temperature sensitive element 164 within tube 166 helps ensure that the measured temperature is precisely that of pH glass electrode 142. This close thermal coupling between element 164 and pH glass electrode 142 helps improve the accuracy of calibration(s) as well as pH measurement.

FIG. 5B is a cross-sectional view showing pH sensor 100 in its storage position. As shown in FIG. 5B, plunger flange 118 is spaced farther from slide lock 120 in FIG. 5B than in FIG. 5A. Further, end 140 is pressed into contact with plunger sleeve 114. Further, storage fill solution cavity 168 is sealed within plunger sleeve 114 via sealing elements (e.g. o-rings) 160 and 170. In this position, pH glass electrode 142 is sealed within storage fill solution cavity 168. Storage fill solution is selected to have a known pH value. Thus, prior to placing pH sensor 100 in its operating position, a calibration operation can be done by causing pH glass electrode to sense the pH of the storage fill solution. The storage fill solution with the known pH value provides the capability of one-point calibration for the pH sensor, thus minimizing error when the pH sensor is placed in its operating position (shown in FIG. 5A).

Figure 6B:
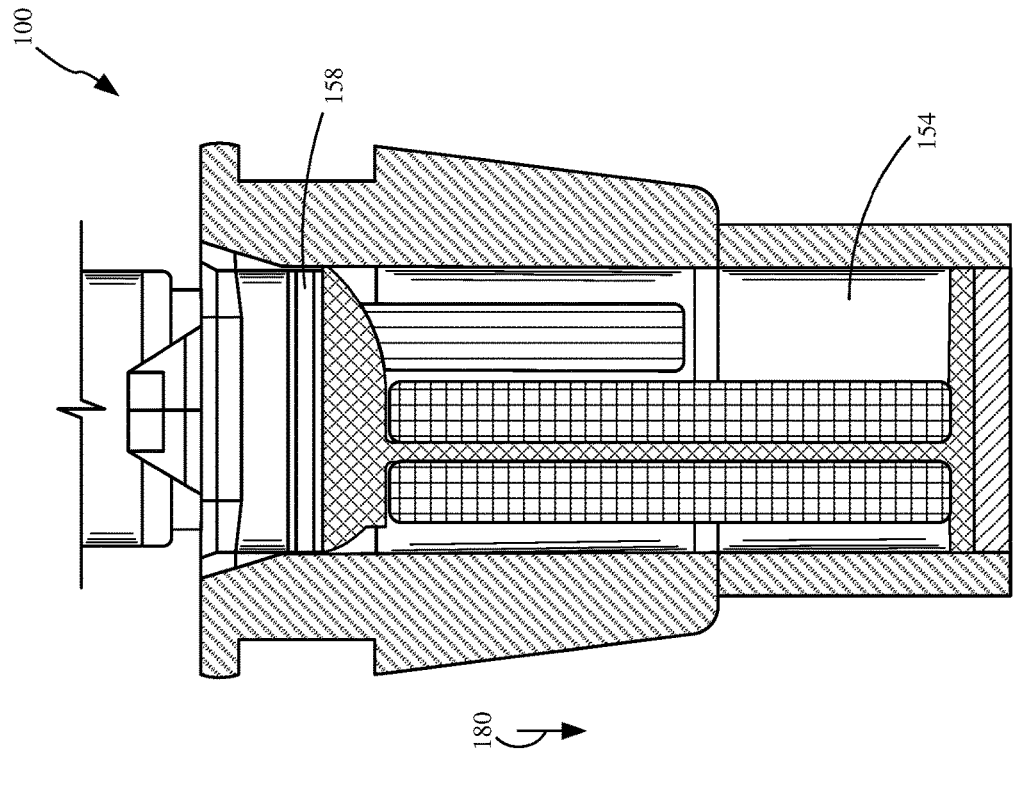
FIGS. 6A and 6B are diagrammatic views of filling the reference fill cavity of a pH sensor in accordance with an embodiment of the present invention.
Figure 6A:
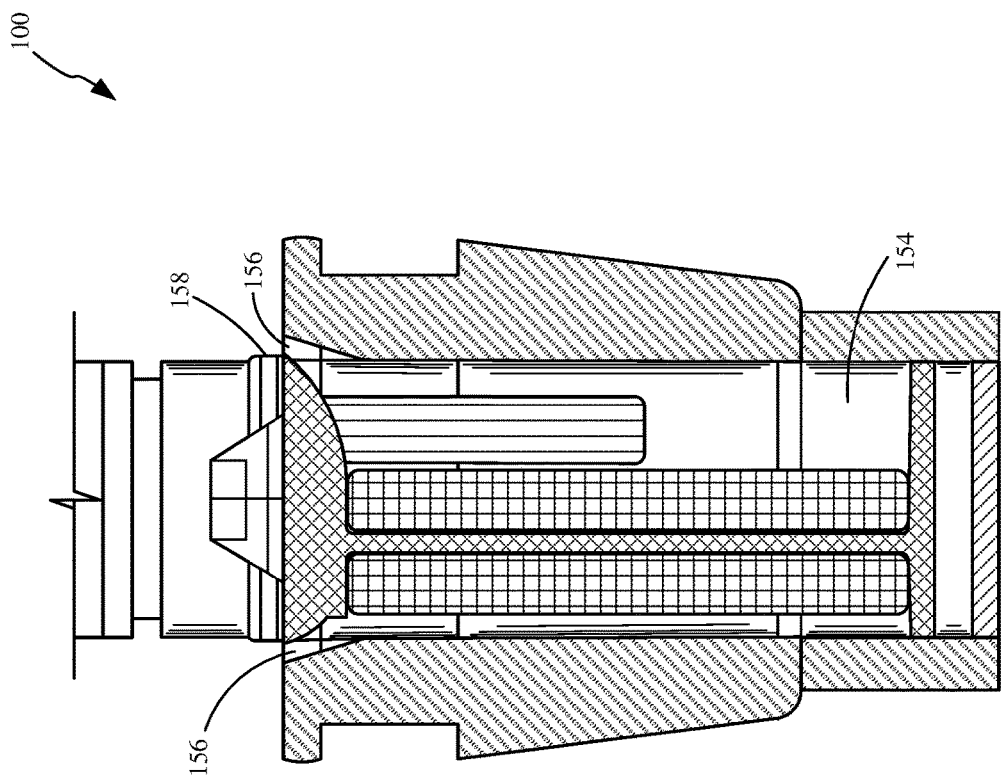

FIGS. 6A and 6B are diagrammatic views of filling the reference fill cavity of a pH sensor in accordance with an embodiment of the present invention. In FIG. 6A, the plunger has been lifted or withdrawn sufficiently to allow O-ring 158 to be located above reference fill channels 156. In this position, reference fill solution can be introduced into reference fill chamber 154. The lower portion of reference fill chamber 154 is still sealed by O-ring 160 (shown in FIGS. 5A and 5B). When a sufficient amount of reference fill solution is introduced into reference fill cavity 154, the plunger is lowered (in the direction shown by arrow 180 in FIG. 6B) until O-ring 158 is located below reference solution fill channels 156. In this position (FIG. 6B) the reference fill solution is sealed within reference fill chamber 154 by O-rings 158, 160. In one example, plunger sleeve 114 is transparent in order to allow a user to observe the filling operation to ensure there are no air bubbles accumulating at the reference junction.

Figure 7C:
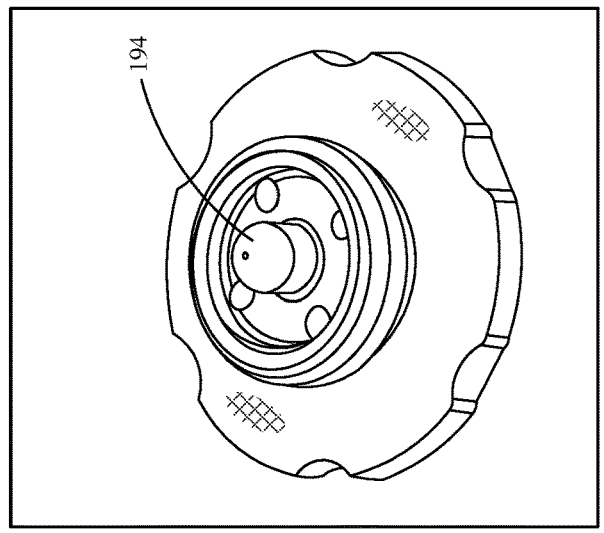
FIG. 7C is a perspective view of a storage cap that can be attached to a pH sensor in accordance with an embodiment of the present invention.
Figure 7B:
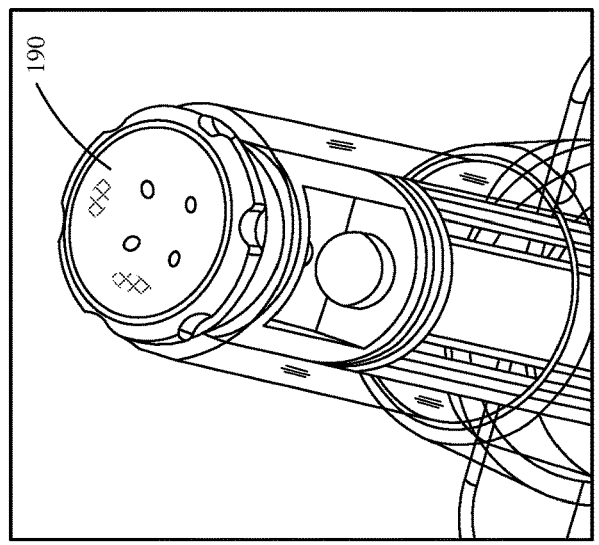
FIGS. 7A and 7B are diagrammatic views illustrating filling a storage fill cavity of a pH sensor through a fill channel in accordance with an embodiment of the present invention.
Figure 7A:
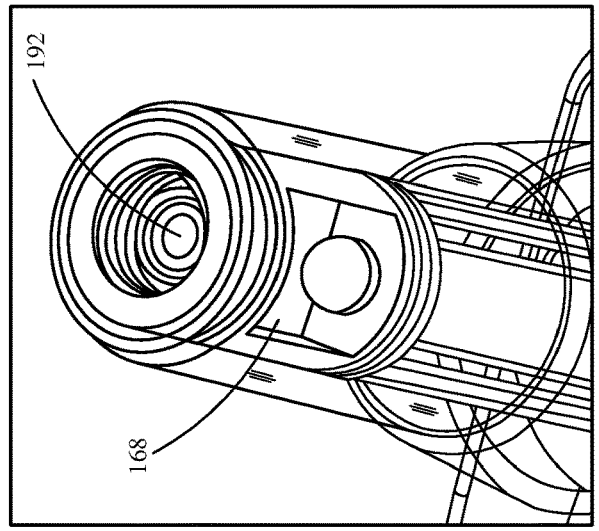
Figure 8:
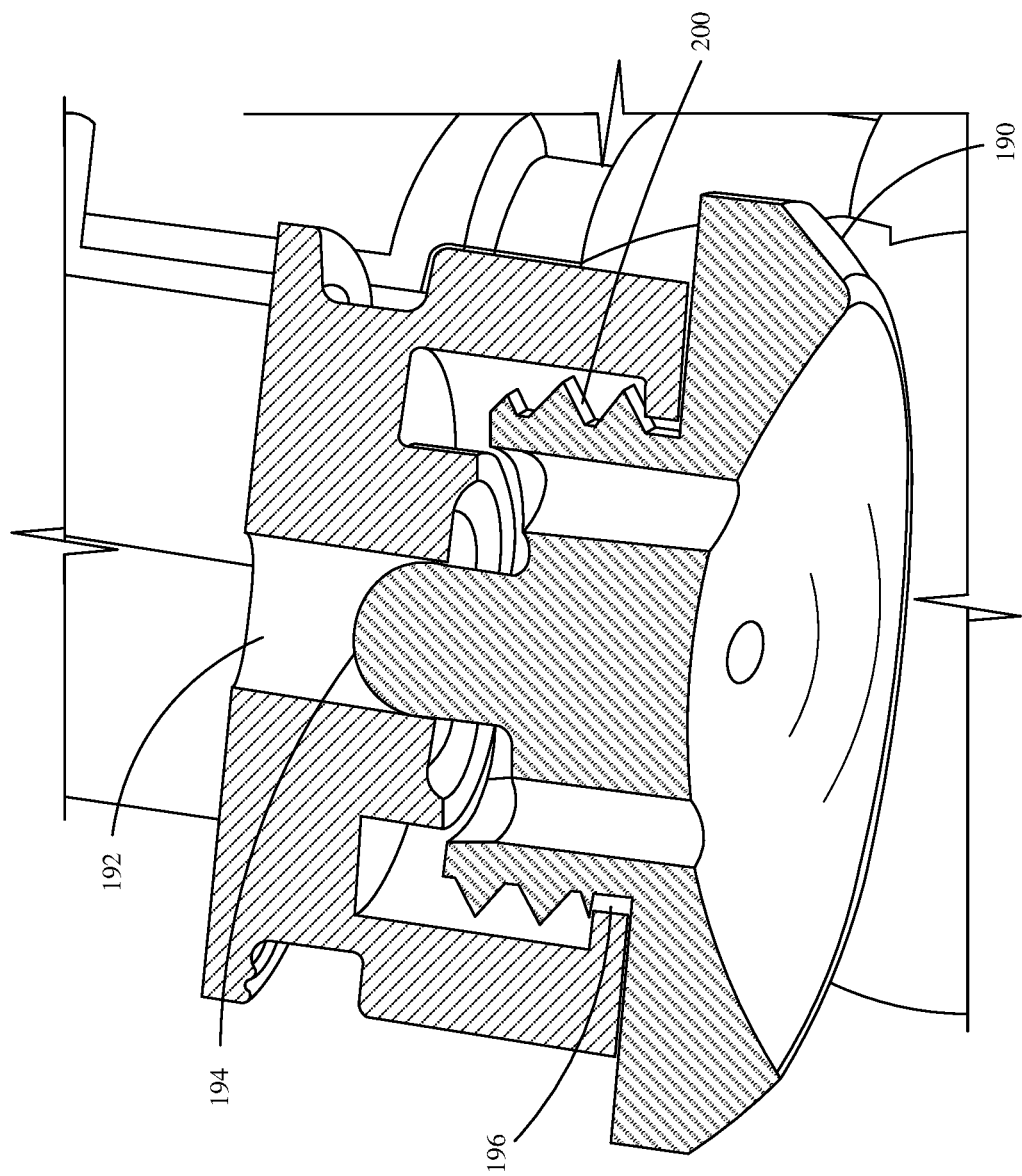
FIG. 8 is a diagrammatic cross-sectional view of an alternative design of a fill cap in accordance with another embodiment of the present invention.

FIGS. 7A and 7B are diagrammatic views illustrating filling a storage fill cavity of a pH sensor through a fill channel in accordance with an embodiment of the present invention. In FIG. 7A, fill cap 190 (shown in FIG. 7B) has been removed allowing access to storage fill cavity 168 via storage fill channel 192. The storage fill solution is injected into storage fill cavity 168 through storage fill channel 192, and then sealed by fill cap 190 with a seal element, such as an O-ring. FIG. 7B illustrates fill cap 190 coupled to pH sensor 100 when storage fill cavity 168 has been filled with storage solution. As shown in FIG. 7C, fill cap 190 contains a seal element (such as plug 194 that is coupled with an O-ring to seal storage fill cavity 168). FIG. 8 shows filling cap 190 engaged such that plug 194 seals fill channel 192. According to one embodiment, FIG. 8 also shows fill cap 190 having a mechanical locking feature 196 on the threads 200 of fill cap 190. This can be done with either a cut in the threads to allow the fill cap 190 to freely spin or only have threads on the cap and not the housing. This would only happen after the required distance is achieved to allow the seal element (plug, or O-ring) to properly seal. Doing this would ensure that fill cap 190 is locked into place without the use of additional epoxies, adhesives, etc. which would be process facing.

Figure 9:
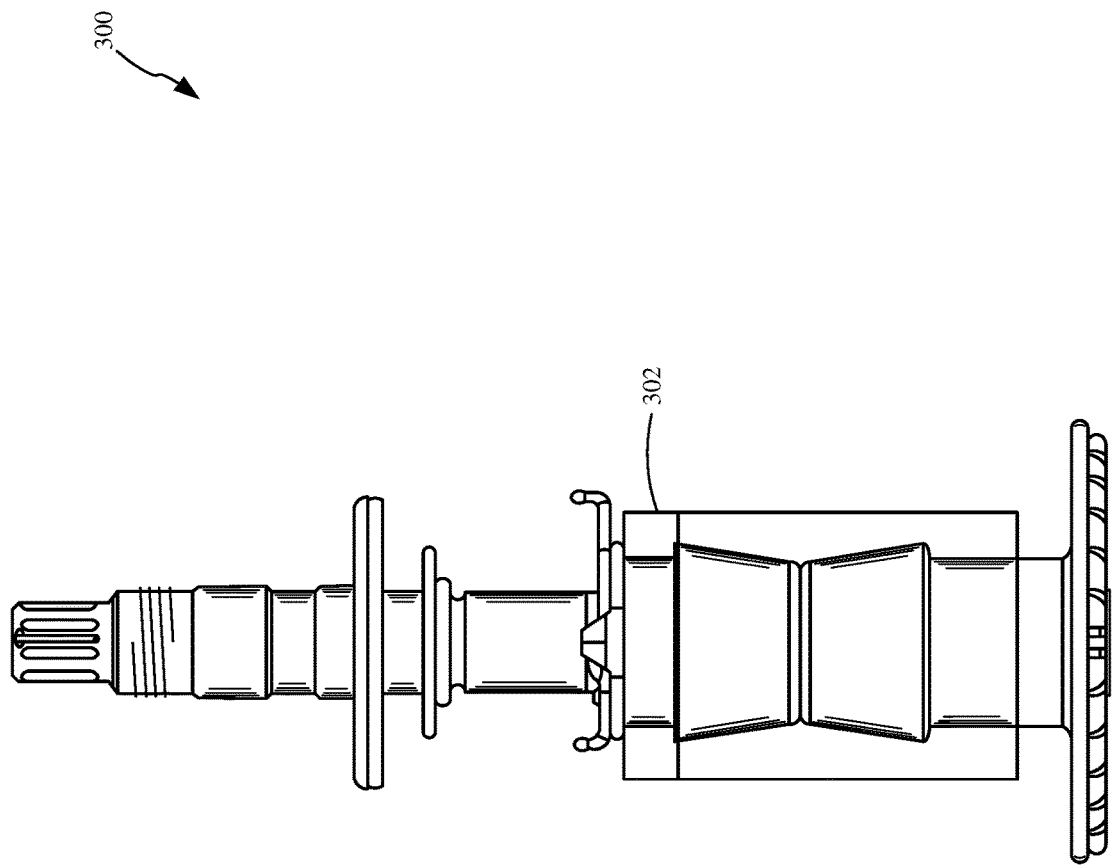
FIG. 9 is a diagrammatic view of an alternate sensor-to-bag interface in accordance with another embodiment of the present invention.

FIG. 9 is a diagrammatic view of an alternate sensor-to-bag interface in accordance with another embodiment of the present invention. In the illustrated example, a mechanical feature 302 has been added to the pH sensor that interacts with the bag manufacture's bioreactor bag flange. Since the bag is pressurized during application, the only connection point of concern is the attachment to the bag. This would eliminate plastic fastening devices (zip tie, etc.) to ensure the sensor is held in place.

Although the present invention has been described with reference to preferred embodiments, workers skilled in the art will recognize that changes may be made in form and detail without departing from the spirit and scope of the invention.

What is claimed is:

1. A pH sensor for a single-use container, the pH sensor comprising:
   a plunger sleeve configured to couple to a flange of the single-use container;
   a plunger axially movable within the plunger sleeve between a filling position, a storage position, and an operating position;
   a reference fill chamber configured to contain a reference fill electrolyte, the reference fill chamber including at least one reference junction;
   a reference electrode operably disposed within the reference fill chamber;
   a pH sending element coupled to the plunger wherein the pH element is disposed within a storage chamber in the storage position and is configured to be exposed to an interior of the single-use container in the operating position; and
   wherein the plunger includes at least one filling channel that allows access to the reference fill chamber when the plunger is in the filling position.

2. The pH sensor of claim 1, and further comprising a seal disposed about the plunger and positioned such that the seal is on a first side of the at least one filling channel when the plunger is in the storage position and on an opposite side of the at least one fill channel when the plunger is in the filling position.

3. The pH sensor of claim 1, wherein the plunger has an end with a storage solution fill channel that is fluidically coupled to the storage solution fill cavity.

4. The pH sensor of claim 3, and further comprising a fill cap sealingly coupled to the end of the plunger to seal the storage solution fill channel.

5. The pH sensor of claim 4, wherein the fill cap includes a mechanical locking feature to lock the fill cap to the end of the plunger.

6. The pH sensor of claim 1, and further comprising a temperature sensitive element disposed within the pH sensor and configured to sense temperature proximate the pH sensing element.

7. The sensor of claim 6, wherein the pH sensitive element is a pH glass bulb.

8. The pH sensor of claim 7, wherein the pH glass bulb is coupled to a glass tube, and the temperature sensitive element is disposed within the glass tube.

9. The pH sensor of claim 6, wherein the temperature sensitive element is an RTD.

10. The pH sensor of claim 6, wherein the temperature sensitive element is a thermocouple.

11. The pH sensor of claim 6, and further comprising a sealed electrical connector operably coupled to the pH sensing element and the temperature sensitive element.

12. The pH sensor of claim 11, wherein the sealed electrical connector is a variopin connector.

13. The pH sensor of claim 1, wherein the reference electrode is a double junction reference electrode.

14. The pH sensor of claim 1, wherein the reference electrode includes a silver wire coated with silver chloride.

15. The pH sensor of claim 1, wherein the at least one reference junction includes a plurality of reference junctions.

16. The pH sensor of claim 15, wherein one reference junction of the plurality of reference junctions is located between the reference fill cavity and a storage fill cavity.

17. The pH sensor of claim 1, wherein the at least one reference junction is formed or a ceramic.

* * * * *